US009492516B2

(12) United States Patent
Admyre et al.

(10) Patent No.: US 9,492,516 B2
(45) Date of Patent: Nov. 15, 2016

(54) METHOD FOR PREVENTION OF COLECTOMY

(71) Applicant: INDEX PHARMACEUTICALS AB, Stockholm (SE)

(72) Inventors: Charlotte Admyre, Vendelsö (SE); Arezou Zargari, Solna (SE); Oliver Von Stein, Upplands Väsby (SE); Petra Von Stein, Upplands Väsby (SE)

(73) Assignee: INDEX PHARMACEUTICALS AB, Stockholm (SE)

( * ) Notice: Subject to any disclaimer, the term of this patent is extended or adjusted under 35 U.S.C. 154(b) by 0 days.

(21) Appl. No.: 14/359,945

(22) PCT Filed: Nov. 23, 2012

(86) PCT No.: PCT/EP2012/073501
§ 371 (c)(1),
(2) Date: May 22, 2014

(87) PCT Pub. No.: WO2013/076262
PCT Pub. Date: May 30, 2013

(65) Prior Publication Data
US 2015/0004187 A1 Jan. 1, 2015

Related U.S. Application Data

(60) Provisional application No. 61/595,230, filed on Feb. 6, 2012.

(30) Foreign Application Priority Data

Nov. 25, 2011 (EP) ..................... 11190826

(51) Int. Cl.
A61K 48/00 (2006.01)
A61K 39/00 (2006.01)
C12N 15/117 (2010.01)

(52) U.S. Cl.
CPC ......... *A61K 39/0005* (2013.01); *C12N 15/117* (2013.01); *C12N 2310/17* (2013.01); *C12N 2310/315* (2013.01)

(58) Field of Classification Search
None
See application file for complete search history.

(56) References Cited

U.S. PATENT DOCUMENTS

| | | | | |
|---|---|---|---|---|
| 6,809,193 B2 * | 10/2004 | McKay | ................ | C07H 21/00 435/325 |
| 2008/0318885 A1 | 12/2008 | Spiik et al. | | |
| 2009/0143319 A1 | 6/2009 | Gemba et al. | | |
| 2010/0234449 A1 * | 9/2010 | Lofberg | ................ | A61K 31/56 514/44 R |
| 2012/0172420 A1 | 7/2012 | Spiik et al. | | |
| 2012/0277293 A1 | 11/2012 | Lofberg et al. | | |

FOREIGN PATENT DOCUMENTS

| | | |
|---|---|---|
| JP | 2008-544983 A | 12/2008 |
| WO | 2006/132204 A1 | 12/2006 |
| WO | WO-2007/004977 A1 | 1/2007 |
| WO | WO-2007/004979 A1 | 1/2007 |
| WO | 2010/053435 A2 | 5/2010 |

OTHER PUBLICATIONS

Bauer, Marc Bacterial CpG-DNA Triggers Activation and Maturation of Human CD11c, CD123+ Dendritic Cells, The Journal of Immunology 2001; pp. 5000-5007; vol. 166; The American Association Immunologists; Bethesda, MD.
Cosnes, Jacques Smoking, Physical Activity, Nutrition & Lifestyle: Environmental Factors & Their Impact on IBD; Digestive Diseases Clinical Review 2010; pp. 411-417; vol. 28; Karger Medical and Scientific Publishers; Switzerland.
Filippi, Jérôme Does Anti-TNF Therapy Reduce the Requirement for Surgery in Ulcerative Colitis? A Systemic Review; Current Drug Targets 2011; pp. 1440-1447; vol. 12, No. 10; Bentham Science Publishers, Ltd.; Oak Park, IL.
Ferrante, Marc Outcome After Proctocolectomy with Ileal Pouch-anal Anastomosis for Ulcerative Colitis; Inflamm Bowel Dis Jan. 2008; pp. 20-28; vol. 14, No. 1; Wiley InterScience (www.interscience.wiley.com).
Geboes, K. A Reproducible Grading Scale for Histological Assessment of Inflammation in Ulcerative Colitis; www.gut.bmj.com 2000; pp. 47:404-9; Pub. By group.bmj.com; UK.
Rachmilewitz, D. Coated Mesalazine (5-aminosalicylic acid) Versus Sulphasalazine in the Treatment of Active Ulcerative Colitis: A Randomised Trial; British Medical Journal Jan. 1998; pp. 82-86; vol. 298; BMJ; UK.
Rubin, David T. Impact of Ulcerative Colitis From Patients' and Physicians' Perspectives: Results from the UC: Normal Survey; Inflammatory Bowel Disease Apr. 2009; pp. 581-588; vol. 15, No. 4; Wiley InterScience (www.interscience.wiley.com).
Sjöberg, Mats Infliximab or Cyclosporine as Rescue Therapy in Hospitalized Patients With Steroid-refractory Ulcerative Colitis: A Retrospective Observational Study; Inflammatory Bowel Disease Feb. 2012; pp. 212-218; vol. 18, No. 2; Wiley Online Library (www.wileyonlinelibrary.com).
Riegler, G. Age-Related Clinical Severity at Diagnosis in 1705 Patients With Ulcerative Colitis; Digestive Diseases and Sciences Mar. 2000; pp. 462-465; vol. 45, No. 3; Springer Science+Business Media; Berlin DE.
Schmitz, Heinz Altered Tight Junction Structure Contributes to the Impaired Epithelial Barrier Function in Ulcerative Colitis; Gastroenterology 1999; pp. 301-309; vol. 116; Elsevier on behalf of the American Gastroenterological Association; Amsterdam NL.

(Continued)

Primary Examiner — Kimberly Chong
(74) Attorney, Agent, or Firm — Porter Wright Morris & Arthur LLP

(57) ABSTRACT

The present invention relates to methods of preventing or reducing the need of colectomy. In particular, the present invention relates to an oligonucleotide, for use in the treatment of an inflammatory bowel disease, such as ulcerative colitis (UC) or Crohn's disease, in a subject that is refractory or responds insufficiently or is intolerant to anti-inflammatory therapy, wherein said oligonucleotide is repetitively administered as a single exposure.

17 Claims, 3 Drawing Sheets

(56) References Cited

OTHER PUBLICATIONS

Thompson, Alexandra I. Genetics of Ulcerative Colitis; Inflammatory Bowel Disease Mar. 2011; pp. 831-848; vol. 17, No. 3; Wiley Online Library (www.wileyonlinelibrary.com).
Langholz, Ebbe Course of Ulcerative Colitis: Analysis of Changes in Disease Activity Over Years; Gastroenterology Jul. 1994; pp. 3-11; vol. 107, No. 1; Elsevier on behalf of American Gastroenterology Association, Amsterdam NL.
Weinryb, Robert M. A Prospective Study of the Quality of Life After Pelvic Pouch Operation; Journal of the American College of Surgeons May 1995; pp. 589-595; vol. 180; Elsevier; Amsterdam NL.
Tokunaga, Tohru Synthetic Oligonucleotides With Particular Base Sequences From the cDNA Encoding Proteins of Mycobacterium bovis BCG Induce Interferons and Activate Natural Killer Cells; Microbiology and Immunology 1992; pp. 55-66; vol. 36, No. 1; Wiley Online Library (www.wileyonlinelibrary.com).
Heller, Frank Oxazolone Colitis, a Th2 Colitis Model Resembling Ulcerative Colitis, Is Mediated by IL-13-Producing NK-T Cells; Immunity Nov. 2002; pp. 629-638; vol. 17; Cell Press; Cambridge, MA.
Klinman, Dennis M. CpG Motifs as Immune Adjuvants; Vaccine 1999; pp. 19-25; vol. 17; Elsevier Science Ltd., Amsterdam NL.
Jahn-Schmid, Beatrice Oligodeoxynucleotides Containing CpG Motifs Modulate the Allergic TH2 Response of BALB/c Mice to Bet v 1, The Major Birch Pollen Allergen; Journal Allergy Clinical Immunology Nov. 1999; pp. 1015-1023; vol. 104, No. 5; Elsevier; Amsterdam NL.
Turner, Dan Response to Corticosteroids in Severe Ulcerative Colitis: A Systematic Review of the Literature and a Meta-Regression; Clinical Gastroenterology and Hepatology 2007; pp. 103-110; vol. 5, No. 1; Elsevier on behalf of American Gastroenterological Association; Amsterdam NL.
Wine, Eytan Adherent-invasive *Escherichis coli* Target the Epithelial Barrier; Gut Microbes Mar./Apr. 2010; pp. 80-84; vol. 1, Issue 2; Landes Bioscience (landesbioscience.com/journals/gutmicrobes/article/11142).
Triantafillidis, John K. Current and Emerging Drugs for the Treatment of Inflammatory Bowel Disease; Drug Design, Development and Therapy 2011; pp. 185-210; vol. 5; Dove Medical Press Ltd.; Princeton, NJ.
Wilhelm, Sheila M. A Review of Infliximab Use in Ulcerative Colitis; Clinical Therapeutics Nov. 2008; pp. 223-230; vol. 30, No. 2; Elsevier; Amsterdam NL.
Xavier, R. J. Unravelling the Pathogenesis of Inflammatory Bowel Disease; Nature Jul. 2007; pp. 427-434; vol. 448; Nature Publishing Group; London, UK.
Krugg, Anne Toll-like Receptor Expression Reveals CpG DNA as a Unique Microbial Stimulus for Plasmacytoid Dendritic Cells Which Synergizes With CD40 Ligand to Induce High Amounts of IL-12; European Journal of Immunology 2001; pp. 3026-3037; vol. 31; Wiley-VCH, Germany.
Tighe, Helen Conjugation of Protein to Immunostimulatory DNA Results in a Rapid, Long-lasting and Potent Induction of Cell-mediated and Humoral Immunity; European Journal of Immunology 2000; pp. 1939-1947; vol. 30; Wiley-VCH, Germany.
Cho, Judy H. Recent Insights Into the Genetics of Inflammatory Bowel Disease; Gastroenterology 2011; pp. 1704-1712; vol. 140, No. 6; Elsevier on behalf of the American Gatroenterological Association Institute; Amsterdam, NL.
International Search Report for PCT/EP2012/073501, ISA/EP, mailed Apr. 25, 2013.
Judy H. Cho et al., "Recent Insights Into the Genetics of Inflammatory Bowel Disease", Gastroenterology, vol. 140, No. 6, May 1, 2011, pp. 1704-1712. E2, XP055020412, ISSN: 0016-5085, DOI:10.1053/j.gastro.2011.02.046.
Petra Von Stein: "Inflammatory bowel disease classification through multigene analysis: fact or fiction?", Expert Review of Molecular Diagnostics, Jan. 2009 LNKD-Pubmed:19099342, vol. 9, No. 1, Jan. 2009, pp. 7-10, XP002670457, ISSN: 1744-8352.
European Medicines Agency, Public summary of opinion on orphan designation, Antisense NF-kBp65 oligonucleotide for the treatment of active ulcerative colitis, Committee for Orphan Medicianal Products, EMA/COMP/1500/2002 REV. 4 (Mar. 10, 2015).
GASTRO, XP-002670456, DIMS0150 as rectal therapy in steroid refractory ulcerative colitis? results rom a placebo controlled randomised trial, Thomson Reuters Integrity, Abst P0357 (Nov. 21-25, 2009).

* cited by examiner

```
SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(19)
<223> OTHER INFORMATION: asterisk (*) indicates phosphorothioate
      modification in positions 1, 2, 3, 16, 17 and 18:
      G*G*A*ACAGTTCGTCCAT*G*G*C
<220> FEATURE:
<221> NAME/KEY: misc_feature
<222> LOCATION: (10)..(11)
<223> OTHER INFORMATION: CG dinucleotide is unmethylated.

<400> SEQUENCE: 1
ggaacagttc gtccatggc                                    19

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(11)
<223> OTHER INFORMATION: GC dinucleotide is unmethylated.

<400> SEQUENCE: 2
ggaacagttc gtccatggc                                    19
```

METHOD FOR PREVENTION OF COLECTOMY

CROSS-REFERENCE TO RELATED APPLICATIONS

This application is a 371 U.S. National Stage of International Application No. PCT/EP2012/073501, filed Nov. 23, 2012, which claims priority to European Patent Application No. 11190826.5, filed Nov. 25, 2011. This application claims the benefit of U.S. Provisional Application No. 61/595,230, filed Feb. 6, 2012. The disclosures of the above applications are incorporated herein by reference.

FIELD OF THE INVENTION

The present invention relates to methods of preventing or reducing the need of colectomy. In particular, the present invention relates to an oligonucleotide, for use in the treatment of an inflammatory bowel disease, such as ulcerative colitis (UC) or Crohn's disease, in a subject that is refractory or responds insufficiently or is intolerant to anti-inflammatory therapy, wherein said oligonucleotide is repetitively administered as a single exposure. Further, the present invention relates to pharmaceutical compositions comprising said oligonucleotide for the prevention or reduction of need of colectomy.

BACKGROUND OF THE INVENTION

Colectomy is the surgical resection of any extent of the large intestine and is often the clinical endpoint intervention for medical indications such as colon cancer and inflammatory bowel disease (IBD), for example UC.

While the understanding of the etiology of UC has grown over the years, the picture emerging is one of a complex interplay between genetic (Cho and Brant, 2011; Thompson and Lees, 2011), microbial (Wine et al., 2010) and environmental factors (Cosnes, 2010) as well as intestinal epithelial function (Schmitz et al., 1999) and mucosal immune system (Heller et al., 2002). No factor alone appears to be sufficient to trigger the development of the disease and the contribution of each individual component may vary between patients (Xavier and Podolsky, 2007). Clinical presentation of UC depends upon the extent and severity of the disease however predominate features includes blood in stool, stool frequency, passage of mucopus and possible abdominal pain (Riegler et al., 2000).

Effective clinical management of active UC requires a comprehensive understanding of the disease extent, the severity and the potential risks and benefits of the available interventions with focus on the induction and maintenance of remission. Corticosteroids remain the cornerstone of initial therapy yet a third of patients will fail to respond, and further management involves critical and timely decisions on whether to use rescue therapy in the form of immunomodulatory drugs such as Ciclosporine A or anti-TNF therapies such as Infliximab (Turner et al., 2007). Current data suggest that rescue with Ciclosprine A and Infliximab are efficacious in the short to medium term perspective (Wilhelm et al., 2008; Filippi et al., 2011) but the long term outcome seems less efficacious (Sjöberg et al., 2011). Furthermore, a significant proportion of UC patients will have recurrent flares or chronic continuous disease despite receiving conventional symptomatic treatment and within a 10 year period, some 20 percent of these patients will require surgical intervention (Langholz et al., 1994).

While surgical intervention may be curative and provide a better quality of life (Weinryb et al., 1995), it is not without considerable risks to the patient (Ferrante et al., 2008) and the procedure itself presents a significant pre- and postoperative morbidity as well as an economic burden to the healthcare system (Rubin et al., 2009). Consequently, there is an urgent need for alternative treatments.

SUMMARY OF THE INVENTION

The present invention relates to methods of preventing or reducing the need of colectomy. In particular, the present invention relates a method, wherein an effective amount of an oligonucleotide comprising the sequence 5'-$X_m$-TTCGT-$Y_n$-3' is administered repetitively as a single exposure to a subject in need thereof, for the prevention of colectomy, wherein X is A, T, C or G, Y is A, T, C or G, m=0-12, n=0-12 and wherein at least one CG dinucleotide is unmethylated. Further the present invention relates to pharmaceutical compositions comprising said oligonucleotide together with one or more pharmaceutically acceptable excipient(s) and/or carrier(s), as well as exposure regimes of said oligonucleotide for preventing or reducing the need of colectomy. In particular, the present invention relates to methods of preventing or reducing the need of colectomy. In particular, the present invention relates to an oligonucleotide, for use in the treatment of an inflammatory bowel disease, such as ulcerative colitis (UC) or Crohn's disease, in a subject that is refractory or responds insufficiently or is intolerant to anti-inflammatory therapy, wherein said oligonucleotide is repetitively administered as a single exposure.

BRIEF DESCRIPTION OF THE FIGURES

These and other aspects of the invention will now be described in further detail, with reference to the appended figures.

DETAILED DESCRIPTION

Figure 1:
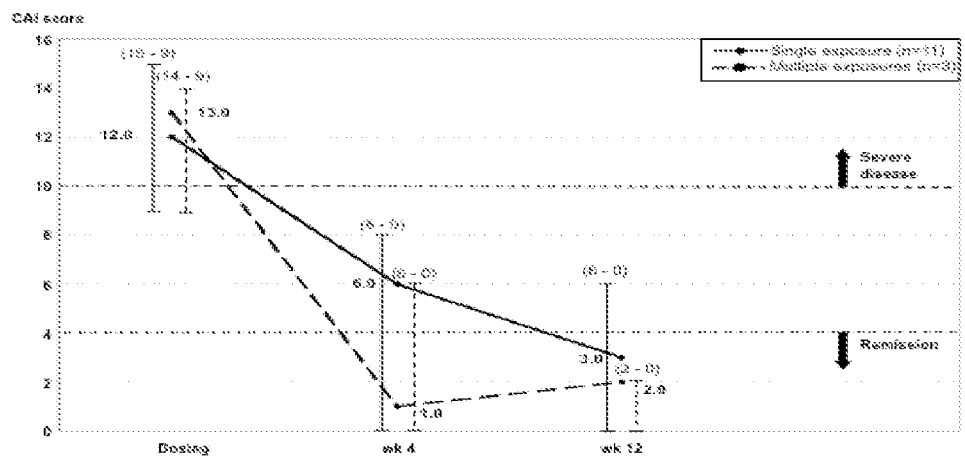
FIG. 1 represents a graph showing the median change in CAI score (bold values) following single exposure (continuous line) or multiple exposures (hatched line) of DIMS0150 (SEQ ID NO:1) therapy. Vertical bars give the range values.

All patents, patent applications, and publications cited herein are hereby incorporated by reference in their entirety.

As used herein, the term inflammatory bowel disease (IBD) refers to a group of inflammatory conditions of the colon and the small intestine. The major types of IBD are UC and Crohn's disease. The main difference between UC and Crohn's disease is the location and nature of the inflammatory changes. Crohn's disease can affect any part of the gastrointestinal tract, from mouth to anus, while UC is most often restricted to the colon and the rectum. In rare cases, a definitive diagnosis of either Crohn's disease or UC cannot be made due to idiosyncrasies in the presentation. In these cases a diagnosis of indeterminate colitis may be made. Other forms of IBD include, but are not limited to, collagenous colitis, lymphocytic colitis, ischaemic colitis, diversion colitis, Behçet's disease and indeterminate colitis.

As used herein, the term "chronic active ulcerative colitis" refers to patients with ulcerative colitis, typically with an active disease of gradual onset, with almost constant diarrhea mixed with blood.

As used herein, the term "colectomy" refers to surgical resection of any extent of the large intestine (colon). Herein, colectomy includes, but is not limited to, right hemicolectomy, left hemicolectomy, extended hemicolectomy, transverse colectomy, sigmoidectomy, proctosigmoidectomy, Hartmann operation, "double-barrel" or Mikulicz colostomy, total colectomy (also known as Lane's Operation), total procto-colectomy and subtotal colectomy.

As used herein, the phrase "elective for colectomy" refers to a subject who may choose to undergo the procedure of non-emergency colectomy based on physician and surgeon assessment. Subjects elective for colectomy may be, but are not limited to, subjects refractory to available therapy or intolerant of available therapy. This differs from emergency colectomy, which is an acute intervention for subjects with acute illnesses or injuries and who require immediate medical attention. The phrase also includes subjects that are elected for colectomy.

References describing immunostimulatory activity of polynucleotides include, but are not limited to, Krug et al. (2001); Bauer et al. (2001); Klinman et al. (1999); Jahn-Schmid et al. (1999) and Tighe et al. (2000).

Further references describing immunostimulatory sequences include: Tokunaga et al. (1992), Yamamoto (1992), EP468520, WO9602555, WO9728259, WO9816247, WO2007004977, WO2007004979, U.S. Pat. No. 6,339,068, U.S. Pat. No. 6,406,705, U.S. Pat. No. 6,426,334 and U.S. Pat. No. 6,426,336.

The term "immunomodulatory response" describes the change of an immune response when challenged with an immunomodulatory oligonucleotide. This change is often measurable through the release of certain cytokines such as interferons as well as other physiological parameters such as proliferation. The response can equally be one that serves to stimulate the immune system as well as to repress the immune system depending on the cytokines induced by the immunomodulatory oligonucleotide in question.

For purposes of the invention, the term "immunomodulatory oligonucleotide" refers to an oligonucleotide as described below that induces an immune response either stimulating the immune system or repressing the immune system or both in an organism when administered to a vertebrate, such as a mammal. As used herein, the term "mammal" includes, without limitation rats, mice, cats, dogs, horses, cattle, cows, pigs, rabbits, non-human primates, and humans.

As used herein, the term "subject" typically refers to human subject/patient. Subjects may, however, be other vertebrate animals, such as mammals.

For purposes of the invention, the term "oligonucleotide" refers to a polynucleoside formed from a plurality of linked individual nucleoside units. Such oligonucleotides can be obtained from existing nucleic acid sources, including genomic DNA or cDNA, plasmids, vectors, or bacterial DNA, but are preferably produced by synthetic methods. The nucleoside residues can be coupled to each other by any of the numerous known internucleoside linkages. Such internucleoside linkages include, without limitation, the natural internucleoside phosphodiester bond or indeed modified internucleosides such as, but not limited to, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkages (e.g., (Rp)- or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers. The alkyl linker may be branched or unbranched, substituted or unsubstituted, and chirally pure or a racemic mixture.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside, an arabinonucleoside or a 2'-deoxy-2'-substituted-arabinoside.

As used herein, the term "a hybrid oligonucleotide" is an oligonucleotide having more than one type of nucleoside.

Herein, the term "oligonucleotide" includes hybrid and chimeric oligonucleotides. A "chimeric oligonucleotide" is an oligonucleotide having more than one type of internucleoside linkage within its sequence structure. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (U.S. Pat. No. 5,635,377 and U.S. Pat. No. 5,366,878).

Herein, the term "oligonucleotide" also includes circularized variants and circular oligonucleotides.

Preferably, the immunomodulatory oligonucleotide comprises at least one naturally occurring phosphodiester, or one modified phosphorothioate, or phosphorodithioate internucleoside linkage, however preferred linkages or indeed backbone modifications including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., (Rp)- or (Sp)-phosphorothioate, alkylphosphonate, or phosphotriester linkages).

The sugar moiety of the nucleoside can be a non-naturally occurring sugar moiety. Herein, a "naturally occurring sugar moiety" is a sugar moiety that occurs naturally as part of a nucleic acid, e.g., ribose and 2'-deoxyribose, and a "non-naturally occurring sugar moiety" is any sugar that does not occur naturally as part of a nucleic acid, but which can be used in the backbone for an oligonucleotide, for example but not limited to hexose. Arabinose and arabinose derivatives are examples of preferred sugar moieties.

Modified or substituted oligonucleotides are often preferred over native forms because of desirable properties such as, for example, enhanced cellular uptake, enhanced affinity for nucleic acid target and increased stability in the presence of nucleases. An oligonucleotide is usually comprised of more than ten (10) and up to one hundred (100) or more deoxyribonucleotides or ribonucleotides, although preferably between about eight (8) and about forty (40), most preferably between about eight (8) and about twenty (20). The exact size will depend on many factors, which in turn depends on the ultimate function or use of the oligonucleotide. The oligonucleotide may be generated in any manner, including chemical synthesis, DNA replication, reverse transcription, or a combination thereof.

In one aspect, the invention provides an oligonucleotide comprising the sequence 5'-$X_m$-TTCGT-$Y_n$-3', for use in the prevention of colectomy in a subject, wherein X is A, T, C or G, Y is A, T, C or G, m=0-12, n=0-12 and wherein at least one CG dinucleotide is unmethylated.

In one embodiment of this aspect, there is provided an oligonucleotide for use in the prevention of colectomy, wherein said oligonucleotide comprises the sequence 5'-$X_m$-CAGTTCGTCCA-$Y_n$-3', wherein X is A, T, C or G, Y is A, T, C or G, m=0-8, n=0-8, and wherein at least one CG dinucleotide is unmethylated.

In another embodiment of this aspect, there is provided an oligonucleotide for use in the prevention of colectomy, wherein at least one nucleotide has a phosphate backbone modification.

In another embodiment of this aspect, there is provided an oligonucleotide for use in the prevention of colectomy, wherein at least one nucleotide has a phosphorothioate or a phosphorodithioate modification.

The phosphorothioate linkages can be illustrated with asterisks (*) in the sequence:
5'-G*G*A*ACAGTTCGTCCAT*G*G*C-3'(SEQ ID NO:1), wherein the CG dinucleotide is unmethylated.

In another embodiment of this aspect, there is provided an oligonucleotide for use in the prevention of colectomy, wherein said oligonucleotide has the sequence 5'-G*G*A*ACAGTTCGTCCAT*G*G*C-3'(SEQ ID NO:1), and wherein the CG dinucleotide is unmethylated.

In another embodiment of this aspect, there is provided an oligonucleotide for use in the prevention of colectomy, wherein said oligonucleotide has the sequence 5'-GGAACAGTTCGTCCATGGC-3' (SEQ ID NO:2), and wherein the CG dinucleotide is unmethylated.

The present invention also provides oligonucleotides for use in methods of the invention, having the sequence: 5'-Xm-CG-$Y_n$-3', wherein X is A, T, C or G, Y is A, T, C or G; m=1-100, n=1-100 and wherein at least one CG dinucleotide is unmethylated. Further, there is provided oligonucleotides for use in methods of the invention, having the sequence: 5'-Xm-CG-$Y_n$-3', wherein X is A, T, C or G, Y is A, T, C or G, m is 1-100 and n is 1-100; m is 1-80 and n is 1-80; m is 1-60 and n is 1-60; m is 1-40 and n is 1-40; m is 1-20 and n is 1-20; m is 1-12 and n is 1-12; m is 1-10 and n is 1-10; m is 1-8 and n is 1-8; m is 1-6 and n is 1-6, and wherein at least one CG dinucleotide is unmethylated.

In another embodiment of this aspect, there is provided an oligonucleotide for use in the prevention of colectomy in a subject, wherein said subject is suffering from an IBD. Said IBD may be chronic active ulcerative colitis. Further, said IBD may be Crohn's disease.

In another embodiment of this aspect, there is provided an oligonucleotide for use in the prevention of colectomy, wherein said subject is refractory or responds insufficiently or is intolerant to anti-inflammatory therapy.

In another embodiment of this aspect, there is provided an oligonucleotide for use in the prevention of colectomy, wherein said oligonucleotide is administered as an add-on to a current therapy.

As used herein, the term "add-on" refers to administering of said oligonucleotides in addition to a current therapy or drug regime, without discontinuing the current therapy or drug regime.

In another embodiment of this aspect, there is provided an oligonucleotide for use in the prevention of colectomy, wherein said oligonucleotide is administered intracolonically. Intracolonical administration may be topical, for example performed during colonoscopy with the aid of a spraying catheter, or other suitable medical equipment, inserted though the colonoscopies biopsy channel. The said oligonucleotide may be delivered to the upper portion of the descending colon or to the transverse region of the colon; however other regions are also possible when suited. Topical administration to other parts of the gastrointestinal tract is also possible. Yet in another embodiment of this aspect, the said oligonucleotides can be administered by any appropriate administration route, such as, but not limited to, inhalation, intranasal, parenteral, oral, intradermal, subcutaneous, vaginal and rectal administration. Further, in certain embodiments, systemic administration of said oligonucleotide may be used.

In another embodiment of this aspect, there is provided an oligonucleotide for use in the prevention of colectomy, wherein said subject is elective for colectomy.

In another embodiment of this aspect, there is provided an oligonucleotide for use in the prevention of colectomy, wherein said colectomy is prevented or delayed, typically for at least 5 months. For example, colectomy may be prevented for 9, 12, 13, 17, 18, 19, 23, 24, 27 or 31 months or longer. Preferably colectomy is prevented indefinitely.

In some embodiments said oligonucleotide is administered in combination with other drugs, for example immunomodulatory drugs or anti-TNF therapy drugs or other suitable drugs. Examples of such drugs include, but are not limited to, glucocorticosteroids, cylclosporine, Infliximab, Adallilumab, natural IFN-β, Decortin, S-Ompeprazol, 5-Asa, Azathioprin, Prednisolon and equivalents thereof.

In some embodiments, said oligonucleotide is administered in combination with one or many steroid drugs, for example corticosteroids and glucocorticosteroids.

For purposes of the invention, the terms "in combination with" and "add-on" mean in the course of treating the same disease in the same patient, and include administering the immunomodulatory oligonucleotide in any order, including simultaneous administration, as well as temporally spaced order of up to several months apart. Such combination therapy may also include one or repetitive administration of single doses or exposures of the immunomodulatory oligonucleotide. For example, the immunomodulatory oligonucleotide may be given to a subject, typically a patient, that has started or is undergoing steroid therapy for an IBD, for example UC or Crohn's disease.

In some embodiments, said oligonucleotides may be administered in combination with an increased dose of one or more immunomodulatory drugs in order for the subject to enter into remission by any means (or as judged by any relevant clinical manifestation), such as CAI score ≤4. In another embodiment, an additional dose(s) of said oligonucleotide may be given to the subject in an instance of relapse, as determined for example by a deterioration of the disease to a CAI score of ≥4 or other relevant clinical manifestation.

The embodiments of the aspect of the use of said oligonucleotide in the prevention of colectomy mentioned above, are also valid for the method aspects of the present invention listed below.

In another aspect of the invention, there is provided a method for preventing colectomy, comprising administering an effective exposure of an oligonucleotide comprising the sequence 5'-$X_m$-TTCGT-$Y_n$-3', to a subject in need thereof, wherein X is A, T, C or G, Y is A, T, C or G, m=0-12, n=0-12, and wherein at least one CG dinucleotide is unmethylated.

The phrase "an effective amount" as used herein relates to an amount sufficient to prevent or reduce the need of colectomy in a subject. For example an amount sufficient to prevent or reduce the need of colectomy for at least 2-3 months, more preferably for at least 5 or 6 months, and even more preferable for longer time. Most preferably colectomy is prevented indefinitely and complete clinical remission is maintained, as defined by a CAI score of 0 or 1, with a concomitant endoscopic score of 0-3, or as judged by other relevant clinical manifestations.

In one embodiment of this aspect, said oligonucleotide comprises the sequence 5'-$X_m$-CAGTTCGTCCA-$Y_n$-3', wherein X is A, T, C or G, Y is A, T, C or G, m=0-8, n=0-8, and wherein at least one CG dinucleotide is unmethylated.

In another embodiment of this aspect, said oligonucleotide has at least one nucleotide which has a phosphate backbone modification.

In another embodiment of this aspect, said oligonucleotide has at least one nucleotide which has a phosphorothioate or a phosphorodithioate modification.

In another embodiment of this aspect, said oligonucleotide has the sequence 5'-GGAACAGTTCGTCCATGGC-3' (SEQ ID NO:2), and wherein the CG dinucleotide is unmethylated.

In another embodiment of this aspect, said oligonucleotide has the sequence 5'-G*G*A*ACAGTTCGTCCAT*G*G*C-3'(SEQ ID NO:1), and wherein the CG dinucleotide is unmethylated.

In another embodiment of this aspect, said subject is suffering from an IBD. Said IBD may be chronic active ulcerative colitis. Further, said IBD may be Crohn's disease.

In another embodiment of this aspect, said subject is refractory or responds insufficiently or is intolerant to anti-inflammatory therapy.

In another embodiment of this aspect, said oligonucleotide is administered as an add-on to a current therapy.

In another embodiment of this aspect, said oligonucleotide is administered topically, such as topically to the mucous membrane.

In another embodiment of this aspect, said oligonucleotide is administered intracolonically. Intracolonical administration may be topical, for example performed during colonoscopy with the aid of a spraying catheter, or other suitable medical equipment, inserted though the colonoscopies biopsy channel. The said oligonucleotide may be delivered to the upper portion of the descending colon or to the transverse region of the colon; however other regions are also possible when suited. Topical administration to other parts of the gastrointestinal tract is also possible. Yet in another embodiment of this aspect, the said oligonucleotides can be administered by any appropriate administration route, such as, but not limited to, inhalation, intranasal, parenteral, oral, intradermal, subcutaneous, vaginal and rectal administration. In certain embodiments of the inventive method, systemic administration of said oligonucleotide may be used.

In another embodiment of this aspect, said subject is elective for colectomy.

In another embodiment of this aspect, the said colectomy is prevented for at least 5 months. For example, colectomy may be prevented for 9, 12, 13, 17, 18, 19, 23, 24, 27 or 31 months or longer. Preferably colectomy is prevented indefinitely.

In another aspect, the invention provides a pharmaceutical composition comprising an oligonucleotide having the sequence 5'-$X_m$-TTCGT-$Y_n$-3', wherein X is A, T, C or G, Y is A, T, C or G, m=0-12, n=0-12, and wherein at least one CG dinucleotide is unmethylated, together with one or more pharmaceutically acceptable excipient(s) and/or carrier(s), for use in the prevention of colectomy.

In one embodiment of this aspect, there is provided a pharmaceutical composition for use in the prevention of colectomy, wherein said oligonucleotide is having the sequence 5'-$X_m$-CAGTTCGTCCA-$Y_n$-3', wherein X is A, T, C or G, Y is A, T, C or G, m=0-8, n=0-8, and wherein at least one CG dinucleotide is unmethylated.

In another embodiment of this aspect, there is provided a pharmaceutical composition for use in the prevention of colectomy, wherein said oligonucleotide has at least one nucleotide which has a phosphate backbone modification.

In another embodiment of this aspect, there is provided a pharmaceutical composition for use in the prevention of colectomy, wherein said oligonucleotide has at least one nucleotide which has a phosphorothioate or a phosphorodithioate modification.

In another embodiment of this aspect, there is provided a pharmaceutical composition for use in the prevention of colectomy, wherein said oligonucleotide has the sequence 5'-GGAACAGTTCGTCCATGGC-3' (SEQ ID NO:2), and wherein the CG dinucleotide is unmethylated.

In another embodiment of this aspect, there is provided a pharmaceutical composition for use in the prevention of colectomy, wherein said oligonucleotide has the sequence 5'-G*G*A*ACAGTTCGTCCAT*G*G*C-3' (SEQ ID NO:1), and wherein the CG dinucleotide is unmethylated.

As used herein, the term "carrier" encompasses any excipient, diluent, filler, salt, buffer, water, stabilizer, solubilizer, lipid, or other material well known in the art for use in pharmaceutical formulations. It will be understood that the characteristics of the carrier, excipient, or diluent will depend on the route of administration for a particular application.

As used herein, the term "pharmaceutically acceptable" refers to a material that does not interfere with the effectiveness of the immunomodulatory oligonucleotide and is compatible with a biological system such as a cell, cell culture, tissue, or organism. Preferably, the biological system is a living organism, such as a vertebrate.

In one embodiment of this aspect, there is provided a pharmaceutical composition for use in the prevention of colectomy, wherein the amount of said oligonucleotide is present in the range from about 0.3 mg to about 100 mg.

In one embodiment of this aspect, there is provided a pharmaceutical composition for use in the prevention of colectomy, wherein the amount of said oligonucleotide is present in the range from about 25 mg to about 60 mg.

In one embodiment of this aspect, there is provided a pharmaceutical composition for use in the prevention of colectomy, wherein the amount of said oligonucleotide present within the said composition is about 30 mg.

The concentration of an immunomodulatory oligonucleotide in a pharmaceutically acceptable mixture will vary depending on several factors, including the dosage of the compound to be administered, the pharmacokinetic characteristics of the compound(s) employed, the age, sex and condition of the patient, as well as the route of administration. Effective amounts of immunomodulatory oligonucleotides for preventing or reducing the need for colectomy in a subject would broadly range between about 0.3 mg to about 100 mg, preferably about 3-30 mg, and most preferably about 30 mg.

As used herein, the term "exposure" refers to an administration of an oligonucleotide, wherein a constant drug dose elicits increasing effects and does not refer to cumulative drug effect.

In one embodiment of this aspect, there is provided a pharmaceutical composition for use in the prevention of colectomy, wherein said composition is repetitively administered as a single exposure.

In another embodiment of this aspect, there is provided a pharmaceutical composition for use in the prevention of colectomy, wherein said composition is repetitively administered as a single exposure on two or more separate occasions.

In another embodiment of this aspect, there is provided a pharmaceutical composition for use in the prevention of colectomy, wherein said composition is repetitively administered as a single exposure on two or more separate occasions 4 to 70 weeks apart.

In another embodiment of this aspect, there is provided a pharmaceutical composition for use in the prevention of colectomy, wherein said composition is repetitively administered as a single exposure on two separate occasions 4 to 8 weeks apart.

In another embodiment of this aspect, there is provided a pharmaceutical composition for use in the prevention of colectomy, wherein said composition is repetitively administered as a single exposure on three separate occasions 4 weeks apart.

In another embodiment of this aspect, there is provided a pharmaceutical composition for use in the prevention of colectomy, wherein the said composition is repetitively administered as a single exposure on two separate occasions 4 weeks apart.

In another embodiment of this aspect, there is provided a pharmaceutical composition for use in the prevention of colectomy, wherein the said composition is administered topically, such as topically to the mucosal membrane.

In another embodiment of this aspect, there is provided a pharmaceutical composition for use in the prevention of colectomy, wherein the said composition is administered intracolonically.

In another aspect, the invention provides a pharmaceutical composition comprising an oligonucleotide having the sequence 5'-$X_m$-TTCGT-$Y_n$-3', wherein X is A, T, C or G, Y is A, T, C or G, $m=0-12$, $n=0-12$, and wherein at least one CG dinucleotide is unmethylated, together with one or more pharmaceutically acceptable excipient(s) and/or carrier(s), for use in the treatment of chronic active ulcerative colitis, wherein the composition is repetitively administered as a single exposure.

In one embodiment of this aspect, there is provided a pharmaceutical composition for use in the treatment of chronic active ulcerative colitis, wherein said oligonucleotide has the sequence 5'-$X_m$-CAGTTCGTCCA-$Y_n$-3', wherein X is A, T, C or G, Y is A, T, C or G, $m=0-8$, $n=0-8$, and wherein at least one CG dinucleotide is unmethylated.

In another embodiment of this aspect, there is provided a pharmaceutical composition for use in the treatment of chronic active ulcerative colitis, wherein said oligonucleotide has at least one nucleotide which has a phosphate backbone modification.

In another embodiment of this aspect, there is provided a pharmaceutical composition for use in the treatment of chronic active ulcerative colitis, wherein said oligonucleotide has at least one nucleotide which has a phosphorothioate or a phosphorodithioate modification.

In another embodiment of this aspect, there is provided a pharmaceutical composition for use in the treatment of chronic active ulcerative colitis, wherein said oligonucleotide has the sequence 5'-GGAACAGTTCGTCCATGGC-3' (SEQ ID NO:2), and wherein the CG dinucleotide is unmethylated.

In another embodiment of this aspect, there is provided a pharmaceutical composition for use in the treatment of chronic active ulcerative colitis, wherein said oligonucleotide has the sequence 5'-G*G*A*ACAGTTCGTCCAT*G*G*C-3' (SEQ ID NO:1), and wherein the CG dinucleotide is unmethylated.

In another embodiment of this aspect, there is provided a pharmaceutical composition for use in the treatment of chronic active ulcerative colitis, wherein said oligonucleotide is administered in amount of from about 0.3 mg to about 100 mg.

In another embodiment of this aspect, there is provided a pharmaceutical composition for use in the treatment of chronic active ulcerative colitis, wherein said oligonucleotide is administered in amount of from about 25 mg to about 60 mg.

In another embodiment of this aspect, there is provided a pharmaceutical composition for use in the treatment of chronic active ulcerative colitis, wherein said oligonucleotide is administered in amount of about 30 mg. In another embodiment of this aspect, there is provided a pharmaceutical composition for use in the treatment of chronic active ulcerative colitis, wherein said composition is repetitively administered as a single exposure.

In another embodiment of this aspect, there is provided a pharmaceutical composition for use in the treatment of chronic active ulcerative colitis, wherein said composition is repetitively administered as a single exposure on two or more separate occasions 4 to 70 weeks apart.

In another embodiment of this aspect, there is provided a pharmaceutical composition for use in the treatment of chronic active ulcerative colitis, wherein said composition is repetitively administered as a single exposure on two separate occasions 4 to 8 weeks apart.

In another embodiment of this aspect, there is provided a pharmaceutical composition for use in the treatment of chronic active ulcerative colitis, wherein said composition is repetitively administered as a single exposure on two separate occasions 4 weeks apart.

In another embodiment of this aspect, there is provided a pharmaceutical composition for use in the treatment of chronic active ulcerative colitis, wherein said composition is repetitively administered as a single exposure on three separate occasions 4 weeks apart.

In another embodiment of this aspect, there is provided a pharmaceutical composition for use in the treatment of Crohn's disease, wherein said oligonucleotide has at least one nucleotide which has a phosphate backbone modification.

In another embodiment of this aspect, there is provided a pharmaceutical composition for use in the treatment of Crohn's disease, wherein said oligonucleotide has at least one nucleotide which has a phosphorothioate or a phosphorodithioate modification.

In another embodiment of this aspect, there is provided a pharmaceutical composition for use in the treatment of Crohn's disease, wherein said oligonucleotide has the sequence 5'-GGAACAGTTCGTCCATGGC-3' (SEQ ID NO:2), and wherein the CG dinucleotide is unmethylated.

In another embodiment of this aspect, there is provided a pharmaceutical composition for use in the treatment of Crohn's disease, wherein said oligonucleotide has the sequence 5'-G*G*A*ACAGTTCGTCCAT*G*G*C-3' (SEQ ID NO:1), and wherein the CG dinucleotide is unmethylated.

In another embodiment of this aspect, there is provided a pharmaceutical composition for use in the treatment of Crohn's disease, wherein said oligonucleotide is administered in amount of from about 0.3 mg to about 100 mg.

In another embodiment of this aspect, there is provided a pharmaceutical composition for use in the treatment of Crohn's disease, wherein said oligonucleotide is administered in amount of from about 25 mg to about 60 mg.

In another embodiment of this aspect, there is provided a pharmaceutical composition for use in the treatment of Crohn's disease, wherein said oligonucleotide is administered in amount of about 30 mg. In another embodiment of this aspect, there is provided a pharmaceutical composition for use in the treatment of Crohn's disease, wherein said composition is repetitively administered as a single exposure.

In another embodiment of this aspect, there is provided a pharmaceutical composition for use in the treatment of Crohn's disease, wherein said composition is repetitively administered as a single exposure on two or more separate occasions 4 to 70 weeks apart.

In another embodiment of this aspect, there is provided a pharmaceutical composition for use in the treatment of Crohn's disease, wherein said composition is repetitively administered as a single exposure on two separate occasions 4 to 8 weeks apart.

In another embodiment of this aspect, there is provided a pharmaceutical composition for use in the treatment of Crohn's disease, wherein said composition is repetitively administered as a single exposure on two separate occasions 4 weeks apart.

In another embodiment of this aspect, there is provided a pharmaceutical composition for use in the treatment of Crohn's disease, wherein said composition is repetitively administered as a single exposure on three separate occasions 4 weeks apart.

The person skilled in the art realizes that the present invention by no means is limited to the preferred embodiments described above. On the contrary, many modifications and variations are possible within the scope of the appended claims.

In another embodiment of this aspect, there is provided a pharmaceutical composition for use in the treatment of chronic active ulcerative colitis, wherein the said composition is administered topically, such as topically to the mucosal membrane.

In another embodiment of this aspect, there is provided a pharmaceutical composition for use in the treatment of Crohn's disease, wherein the said composition is administered topically, such as topically to the mucosal membrane.

In another embodiment of this aspect, there is provided a pharmaceutical composition for use in the treatment of chronic active ulcerative colitis, wherein the said composition is administered intracolonically.

In another embodiment of this aspect, there is provided a pharmaceutical composition for use in the treatment of Crohn's disease, wherein the said composition is administered intracolonically.

In another aspect of the invention, there is provided an oligonucleotide comprising the sequence 5'-GGAACAGTTCGTCCATGGC-3' (SEQ ID NO:2), wherein at least one CG dinucleotide is unmethylated, for use in the treatment of an inflammatory bowel disease in a subject that is refractory or responds insufficiently or is intolerant to anti-inflammatory therapy, wherein said oligonucleotide is repetitively administered as a single exposure.

In another embodiment of this aspect, there is provided an oligonucleotide for use, wherein at least one nucleotide in said oligonucleotide has a backbone modification. Typically, said backbone modification is a phosphate backbone modification, represented by a phosphorothioate or a phosphorodithioate modification. Further, said phosphate backbone modification is preferably located in the 5'- and/or the 3'-end of said oligonucleotide.

In another embodiment of this aspect, there is provided an oligonucleotide for use, wherein said oligonucleotide has the sequence 5'-G*G*A*ACAGTTCGTCCAT*G*G*C-3' (SEQ ID NO:1), wherein the CG dinucleotide is unmethylated.

In another embodiment of this aspect, there is provided an oligonucleotide for use, wherein said inflammatory bowel disease is ulcerative colitis.

In another embodiment of this aspect, there is provided an oligonucleotide for use, wherein said inflammatory bowel disease is chronic active ulcerative colitis In another embodiment of this aspect, there is provided an oligonucleotide for use, wherein said inflammatory bowel disease is Crohn's disease.

In another embodiment of this aspect, there is provided an oligonucleotide for use, wherein said oligonucleotide is repetitively administered as a single exposure on two or more separate occasions 4 or more weeks apart.

In another embodiment of this aspect, there is provided an oligonucleotide for use, wherein said oligonucleotide is repetitively administered as a single exposure on separate occasions 4 to 8 weeks apart.

In another embodiment of this aspect, there is provided an oligonucleotide for use, wherein said oligonucleotide is repetitively administered as a single exposure on three separate occasions 4 weeks apart.

In another embodiment of this aspect, there is provided an oligonucleotide for use, wherein said oligonucleotide is repetitively administered as a single exposure on two separate occasions 4 weeks apart.

In another embodiment of this aspect, there is provided an oligonucleotide for use, wherein the amount of said oligonucleotide is present in the range from about 0.3 mg to about 100 mg, preferably in the range from about 25 mg to about 60 mg, more preferably in an amount of about 30 mg.

In another embodiment of this aspect, there is provided an oligonucleotide for use, wherein said oligonucleotide is administered as an add-on to a current therapy.

In another embodiment of this aspect, there is provided an oligonucleotide for use, wherein said oligonucleotide is administered topically to mucosal membranes.

In another embodiment of this aspect, there is provided an oligonucleotide for use, wherein said oligonucleotide is administered intracolonically.

In another embodiment of this aspect, there is provided an oligonucleotide for use, wherein said subject is elective for colectomy. Typically, said colectomy is prevented or delayed.

In another aspect of the invention, there is provided a pharmaceutical composition comprising the sequence 5'-GGAACAGTTCGTCCATGGC-3' (SEQ ID NO:2) and wherein at least one CG dinucleotide is unmethylated, together with one or more pharmaceutically acceptable excipient(s) and/or carrier(s), for use in the treatment of an inflammatory bowel disease in a subject that is refractory or responds insufficiently or is intolerant to anti-inflammatory therapy, wherein said composition is repetitively administered as a single exposure.

In one embodiment of this aspect, there is provided a composition for use, wherein at least one nucleotide in said oligonucleotide has a backbone modification. Typically, said backbone modification is a phosphate backbone modification, represented by a phosphorothioate or a phosphorodithioate modification. Further, said phosphate backbone modification is preferably located in the 5'- and/or the 3'-end of said oligonucleotide.

In another embodiment of this aspect, there is provided a composition for use, wherein said oligonucleotide has the sequence 5'-G*G*A*ACAGTTCGTCCAT*G*G*C-3' (SEQ ID NO:1), wherein the CG dinucleotide is unmethylated.

In another embodiment of this aspect, there is provided a composition for use, wherein said inflammatory bowel disease is ulcerative colitis.

In another embodiment of this aspect, there is provided a composition for use, wherein said inflammatory bowel disease is chronic active ulcerative colitis.

In another embodiment of this aspect, there is provided a composition for use, wherein said inflammatory bowel disease is Crohn's disease.

In another embodiment of this aspect, there is provided a composition for use, wherein said composition is repetitively administered as a single exposure on two or more separate occasions 4 or more weeks apart.

In another embodiment of this aspect, there is provided a composition for use, wherein said composition is repetitively administered as a single exposure on separate occasions 4 to 8 weeks apart.

In another embodiment of this aspect, there is provided a composition for use, wherein said composition is repetitively administered as a single exposure on three separate occasions 4 weeks apart.

In another embodiment of this aspect, there is provided a composition for use, wherein said composition is repetitively administered as a single exposure on two separate occasions 4 weeks apart.

In another embodiment of this aspect, there is provided a composition for use, wherein the amount of said oligonucleotide is present in the range from about 0.3 mg to about 100 mg, preferably from about 25 mg to about 60 mg, more preferably about 30 mg.

In another embodiment of this aspect, there is provided a composition for use, wherein said composition is administered as an add-on to a current therapy.

In another embodiment of this aspect, there is provided a composition for use, wherein said composition is administered topically to mucosal membranes.

In another embodiment of this aspect, there is provided a composition for use, wherein said composition is administered intracolonically.

In another embodiment of this aspect, there is provided a composition for use, wherein said subject is elective for colectomy. Typically, said colectomy is prevented or delayed.

In another aspect of the invention, there is provided a method of treating an inflammatory bowel disease in a subject that is refractory or responds insufficiently or is intolerant to anti-inflammatory therapy, comprising administering to a patient in need thereof, an effective exposure of an oligonucleotide comprising the sequence 5'-GGAACAGTTCGTCCATGGC-3'(SEQ ID NO:2) and wherein at least one CG dinucleotide is unmethylated, wherein said oligonucleotide is repetitively administered as a single exposure.

In one embodiment of this aspect, at least one nucleotide in said oligonucleotide has a backbone modification. Typically, said backbone modification is a phosphate backbone modification, represented by a phosphorothioate or a phosphorodithioate modification. Further, said phosphate backbone modification is preferably located in the 5'- and/or the 3'-end of said oligonucleotide.

In another embodiment of this aspect, said oligonucleotide has the sequence 5'-G*G*A*ACAGTTCGTCCAT*G*G*C-3'(SEQ ID NO:1), wherein the CG dinucleotide is unmethylated.

In another embodiment of this aspect, said inflammatory bowel disease is ulcerative colitis.

In another embodiment of this aspect, said inflammatory bowel disease is chronic active ulcerative colitis.

In another embodiment of this aspect, said inflammatory bowel disease is Crohn's disease.

In another embodiment of this aspect, said oligonucleotide is repetitively administered as a single exposure on two or more separate occasions 4 or more weeks apart.

In another embodiment of this aspect, said oligonucleotide is repetitively administered as a single exposure on separate occasions 4 to 8 weeks apart.

In another embodiment of this aspect, said oligonucleotide is repetitively administered as a single exposure on three separate occasions 4 weeks apart.

In another embodiment of this aspect, said oligonucleotide is repetitively administered as a single exposure on two separate occasions 4 weeks apart.

In another embodiment of this aspect, the amount of said oligonucleotide is in the range from about 0.3 mg to about 100 mg, preferably, from about 25 mg to about 60 mg more preferably about 30 mg.

In another embodiment of this aspect, said composition is administered as an add-on to a current therapy.

In another embodiment of this aspect, said oligonucleotide is administered topically to mucosal membranes.

In another embodiment of this aspect, said oligonucleotide is administered intracolonically.

In another embodiment of this aspect, said subject is elective for colectomy. Typically, said colectomy is prevented or delayed.

EXAMPLES

Patient Selection

Over the course of two and a half years 14 chronic active UC out-patients were treated with DIMS0150 (SEQ ID NO:1) as add-on to their current therapies with 3 subjects receiving 3 doses of DIMS0150 (SEQ ID NO:1) with 4 weeks between exposure occasions. A diagnosis of UC was established in all patients based on clinical, endoscopic and histological features. All patients were judged as being therapy failures with a documented history of not responding adequately to effective dosing regimens of available therapies including high dose i.v glucocorticoids and were considered for elective colectomy based on the treating physician and surgeon's assessment. Base line characteristics are given in Table 1. Subjects who were deemed likely to require prompt clinical intervention or cases of expected colectomy were not considered.

Safety and Efficacy

The suitability of DIMS0150 (SEQ ID NO:1) was evaluated as a potential rescue therapy to prevent colectomy, on a midterm basis of 6 months, if colectomy was elected as the preferred therapy option. Other objectives addressed response (a decrease in CAI score by units from baseline) or remission (CAI score of points) and the prevention of colectomy on a long term basis of more than 6 months.

TABLE 1

Demographic Overview of the Patients

| Patient | Age | Sex | Disease Duration | Disease Extent | Therapy History | Current Medication |
|---|---|---|---|---|---|---|
| p1 | 30 | female | >3 years | Pancolitis | Intolerant to GCS; refractory to Infliximab, Adalilumab; natural IFN-β | Azathioprin 50 mg/day, 5-Asa 4 g/day |
| p2 | 22 | male | 6 years | Pancolitis | Refractory to GCS, Infliximab, Adalilumab, natural IFN-β | Decortin 20 mg/day, S-Ompeprazol 20 mg/day |
| p3 | 44 | male | 20 years | Colitis of rest colon after hemicolectomy (ano-50 cm) | Refractory to GCS and Infliximab | Decortin 40 mg/day, 5-Asa 4 g/day |
| p4 | 68 | male | 1 year | Ulcerative colitis (ano-80 cm) | Refractory to GCS | Decortin 30 mg/day, 5-Asa 4.5 g/day |
| p5 | 45 | male | 4 years | Pancolitis | Refractory to GCS, Infliximab, natural IFN-β | Decortin 35 mg/day, 5-Asa 3 g/day |
| p6 | 54 | female | 4 years | Proctitis (ano-15 cm) | Refractory to GCS and Infliximab | 5-Asa 4 g/day |
| p7 | 74 | female | >3 years | Proctitis (ano-20 cm) | Refractory to GCS | 5-Asa 1.5 g/day |
| p8 | 46 | female | 29 years | Ulcerative colitis (ano-80 cm) | Refractory to GCS | Decortin 10 mg/day, Azathioprin 125 mg/day |
| p9 | 60 | male | >3 years | Ulcerative colitis (ano-60 cm) | Intolerant to GCS; refractory to Infliximab | 5-Asa 2 g/day |
| p10 | 27 | male | 4 years | Ulcerative colitis (ano-60 cm) | Refractory to GCS and Infliximab | Decortin 20 mg/day, Azathioprin 150 mg/day, 5-Asa 4 g/day |
| p11 | 46 | female | 25 years | Proctosigmoiditis (ano-35 cm) | Refractory to GCS | Decortin 10 mg/day, Azathioprin 100 mg/day |
| p12* | 50 | male | 5 years | Pancolitis | Refractory to GCS, Infliximab, natural IFN-β | Decortin 25 mg/day |
| p13* | 36 | female | 7 years | Ulcerative colitis (ano-70 cm) | Refractory to GCS and intolerant to immune suppressants | Decortin 40 mg/day |
| p14* | 50 | female | 2 years | Ulcerative colitis (ano-110 cm) | Refractory to GCS | Decortin 40 mg/day, Azathioprin 100 mg/day |

*Subjects received three exposures of DIMS0150 (SEQ ID NO: 1). Data compiled from August 2008 to March 2011.

Endoscopy was assessed according to the Rachmilewitz composed activity index (Rachmilewitz, 1989) scale (0-12) where endoscopic response was defined as a decrease of ≥4 units from baseline and complete endoscopic remission is represented by 0-3. Histological assessments were made in accordance to the Geboes et al., (2000) scale (0-5) where a response was defined as a decrease of ≥3 units from baseline and complete resolution is indicated by a score of zero. Complete remission was defined as a CAI score of 0 or 1, with a concomitant endoscopic score of 0-3. Clinical assessment of the efficacy parameters were made at weeks 1, 4 and 12. Those patients that received additional exposure(s) of DIMS1050 (SEQ ID NO:1) due to a relapse of symptoms were likewise evaluated at weeks 1, 4 and 12. For all visit occasions, adverse events were recorded.

Therapy

Eleven patients received a single intracolonical administration of 30 mg of DIMS0150 (SEQ ID NO:1) diluted in 50 mL of sterile water in addition to their current therapies. Application of drug was performed during colonoscopy with the aid of a spraying catheter inserted through the colonoscopies biopsy channel and delivered approximately to the upper portion of the descending colon or to the transverse region. In instances of a relapse (as determined by a deterioration of the disease of CAI units) an additional exposure(s) of DIMS0150 (SEQ ID NO:1) was offered and the patient subsequently followed.

Figure 2:
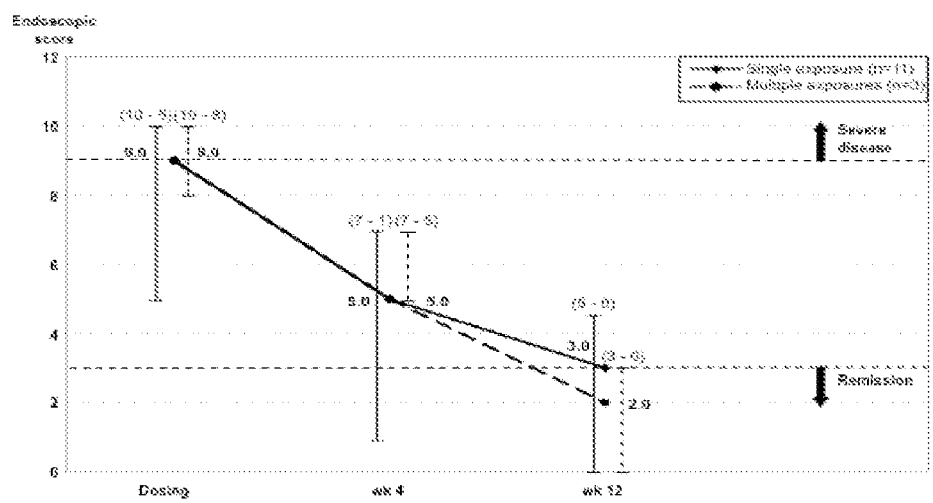
FIG. 2 represents a graph showing median change in endoscopic score according to Rachmilewitz et. al, (bold values) following single exposure (continuous line) or multiple exposures (hatched line) of DIMS0150 (SEQ ID NO:1) therapy. Vertical bars give the range values.
Figure 3:
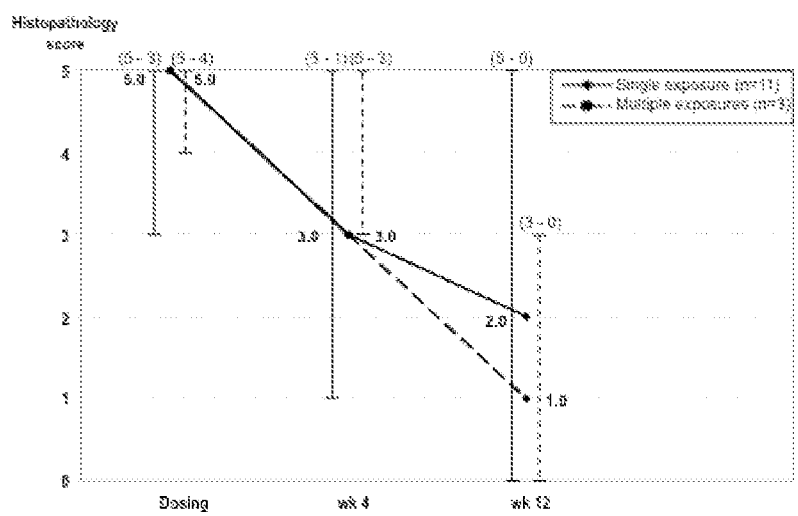
FIG. 3 represents a graph showing median change in histological score according to Geboes et. al, (bold values) following single exposure (continuous line) or multiple exposures (hatched line) of DIMS0150 (SEQ ID NO:1) therapy. Vertical bars give the range values.
Figure 4:
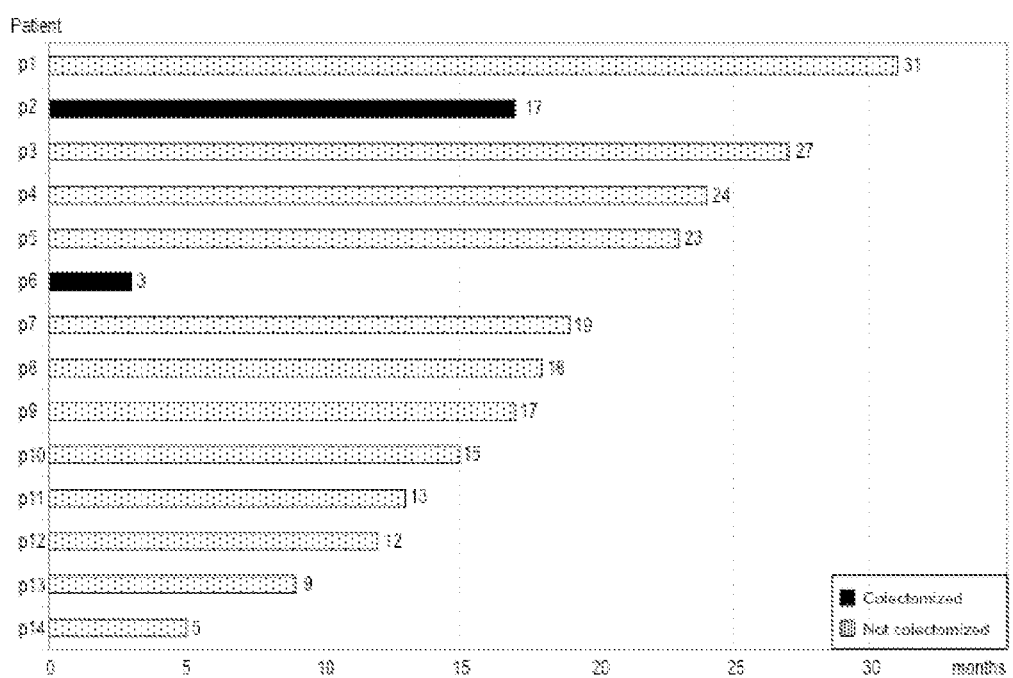
FIG. 4 represents a graph showing the length of colectomy-free period following DIMS0150 (SEQ ID NO:1) therapy. Black bars represent colectomized patients. Data compiled from August 2008 to March 2011.

Three patients received 3 doses of DIMS0150 (SEQ ID NO:1) at 4 weeks intervals. Table 2 outlines patient's base-line characteristics and clinical response parameters, at weeks 1, 4 and 12 and time of additional exposure(s) in those subjects who experienced a relapse.

endoscopic remission. By week 12, an endoscopic response was seen in 73% (8/11) of patients with 45% (5/11) in remission. FIG. 2 illustrates the median endoscopic scores across the 12 week period. Of those subjects receiving a single or multiple exposures to SEQ ID NO:1. For histological evaluation, three biopsy specimens representing three colonic regions (ascending, transverse and descending, respectively) were assessed and the scores are given in Table 2. At week four 18% (2/11) of patients had a histological response and by week 12 this value had increased to 36% (4/11) with 9% (1/11) in histological remission (see Table 3). FIG. 3 illustrates the median histological scores between single and multiple exposures groups across the 12 week period. Five patients (p1-p5) were given additional exposures of DIMS0150 (SEQ ID NO:1) due to a relapse of symptoms at the times indicated (Table 2). All subjects had an improvement in their CAI scores following further therapy with DIMS0150. As a consequence to responding to DIMS0150 all, with the exception of two patients, had so far avoided the need for colectomy (FIG. 4), with the longest period being currently around 40 months (as of end of 2011). Despite initially responding to DIMS0150 (SEQ ID NO:1), patients (p2 and p6) decided to undergo colectomy some 17 and 3 months after first therapy respectively.

TABLE 2

Disease Activity Overview of Patients

| Patient | Disease Activity at Dosing | | | Disease Activity at 4 wks | | | Disease Activity at 12 wks | | | Time point(s) of additional DIMS0150 exposure | Follow-up |
|---|---|---|---|---|---|---|---|---|---|---|---|
| | CAI | Endo | Histo | CAI | Endo | Histo | CAI | Endo | Histo | | |
| p1 | 15 | 10 | 5 | 8 | 8 | 4 | 3 | 2 | 2 | 4 mths | 31 mths |
| p2 | 10 | 10 | 5 | 0 | 5 | 5 | 4 | 4 | 5 | 6 and 12 mths | Colectomized after 17 mths |
| p3 | 14 | 9 | 5 | 4 | 3 | 2 | 5 | 5 | 3 | 5, 10, 20, 23 and 26 mths | 27 mths |
| p4 | 13 | 10 | 3 | 6 | 3 | 3 | 1 | 0 | 1 | 11 mths | 24 mths |
| p5 | 12 | 10 | 5 | 4 | 1 | 3 | 2 | 1 | 2 | 16, 17 and 18 mths* | 23 mths |
| p6 | 14 | 10 | 5 | 8 | 7 | 5 | | | | | Colectomized after 3 mths |
| p7 | 12 | 9 | 5 | 5 | 5 | 4 | 2 | 5 | 4 | | 19 mths |
| p8 | 11 | 9 | 5 | 6 | 5 | 1 | 4 | 4 | 0 | | 18 mths |
| p9 | 9 | 7 | 3 | 7 | 5 | 3 | 4 | 2 | 1 | | 17 mths |
| p10 | 10 | 9 | 5 | 6 | 5 | 4 | 0 | 2 | 1 | | 15 mths |
| p11 | 9 | 5 | 3 | 6 | 5 | 3 | 6 | 5 | 3 | | 13 mths |
| p12* | 9 | 8 | 5 | 1 | 5 | 3 | 0 | 0 | 0 | 4 and 8 weeks | 12 mths |
| p13* | 13 | 9 | 5 | 4 | 7 | 3 | 2 | 3 | 1 | 4 and 8 weeks | 9 mths |
| p14* | 14 | 10 | 4 | 0 | 5 | 5 | 2 | 2 | 2 | 4 and 8 weeks | 5 mths |

*Subjects received 3 exposures of SEQ ID NO: 1 with 4 weeks between each exposure. Data compiled from August 2008 to March 2011

Single Exposure

After therapy with DIMS0150 (SEQ ID NO:1), 73% (8/11) of patients had a clinical response and 27% (3/11) were in remission by week 4. At week 12, clinical response and remission rates were 91% (10/11) and 73% (8/11) respectively, with 2 cases of complete clinical remission. FIG. 1 illustrates the median CAI score observed in those subjects receiving a single or multiple exposures across the 12 week period.

Endoscopic evaluation at week 4, showed that 64% (7/11) of subjects had a endoscopic response with 27% (3/11) in Multiple Exposures Three patients (p12-14)) were administered three exposures of 30 mg DIMS0150 (SEQ ID NO:1) as add-on to current therapies with 4 week intervals between each exposure. The clinical response parameters are provided in Table 3 and interestingly there is a clear improvement in the efficacy parameters at 12 weeks when compared to those values achieved with just a single exposure. This improvement is also evident from FIGS. 2, 3 and 4. Considered collectively, the data seen between the two groups of subjects suggests that multiple exposures with a time frame of 4 weeks between exposures resulted in an improved clinical outcome.

TABLE 3

Rates of disease activity measurements

|  | Clinical response | | Clinical remission | |
| --- | --- | --- | --- | --- |
|  | 4 wks | 12 wks | 4 wks | 12 wks |
| Single Exposure (n = 11) | 73% (8/11) | 91% (10/11) | 27% (3/11) | 73% (8/11) |
| Multiple Exposures (n = 3) | 100% (3/3) | 100% (3/3) | 100% (3/3) | 100% (3/3) |

|  | Endoscopic response | | Endoscopic remission | |
| --- | --- | --- | --- | --- |
|  | 4 wks | 12 wks | 4 wks | 12 wks |
| Single Exposure (n = 11) | 64% (7/11) | 73% (8/11) | 27% (3/11) | 45% (5/11) |
| Multiple Exposures (n = 3) | 33% (1/3) | 100% (3/3) | 0% (0/3) | 100% (3/3) |

|  | Histological response | | Histological remission | |
| --- | --- | --- | --- | --- |
|  | 4 wks | 12 wks | 4 wks | 12 wks |
| Single Exposure (n = 11) | 18% (2/11) | 36% (4/11) | 0% (0/11) | 9% (1/11) |
| Multiple Exposures (n = 3) | 0% (0/3) | 67% (2/3) | 0% (0/3) | 33% (1/3) |

REFERENCES

Bauer M, Redecke V, Ellwart J W, Scherer B, Kremer J P, Wagner H, Lipford G B. Bacterial CpG-DNA triggers activation and maturation of human CD11c−, CD123+ dendritic cells. J Immunol 166, 2001.

Cho J H, Brant S R. Recent insights into the genetics of inflammatory bowel disease. Gastroenterology 2011; 140: 1704-1712.

Cosnes J. Smoking, physical activity, nutrition and lifestyle: environmental factors and their impact on IBD. Dig Dis 2010; 28:411-7.

Filippi J, Allen P B, Hébuterne X, Peyrin-Biroulet L. Does Anti-TNF Therapy Reduce the Requirement for Surgery in Ulcerative Colitis? A Systematic Review. Curr Drug Targets 2011 Apr. 5.

Ferrante M, Declerck S, De Hertogh G, et al. Outcome after proctocolectomy with ileal pouchenanal anastomosis for ulcerative colitis. Inflamm Bowel Dis 2008; 14:20-8.

Geboes K, Riddell R, Ost A, Jensfelt B, Persson T, Lofberg R. A reproducible grading scale for histological assessment of inflammation in ulcerative colitis (comment). Gut 2000; 47:404-409.

Heller F, Fuss I J, Nieuwenhuis E E, Blumberg R S, Strober W. Oxazolone colitis, a Th2 colitis model resembling ulcerative colitis, is mediated by IL-13-producing NK-T cells. Immunity 2002; 17:629-638.

Jahn-Schmid B, Wiedermann U, Bohle B, Repa A, Kraft D, Ebner C. Oligodeoxynucleotides containing CpG motifs modulate the allergic TH2 response of BALB/c mice to Bet v 1, the major birch pollen allergen. J Allergy Clin Immunol. 1999 November; 104(5): 1015-23.

Klinman D M, Barnhart K M, Conover J. CpG motifs as immune adjuvants. Vaccine. 1999 January; 17(1): 19-25.

Krug A, Towarowski A, Britsch S, Rothenfusser S, Hornung V, Bals R, Giese T, Engelmann H, Endres S, Krieg A M, Hartmann G. Toll-like receptor expression reveals CpG DNA as a unique microbial stimulus for plasmacytoid dendritic cells which synergizes with CD40 ligand to induce high amounts of IL-12. Eur J. Immunol. 2001 October; 31(10):3026-37.

Langholz E, Munkholm P, Davidsen M, Binder V. Course of ulcerative colitis: analysis of changes in disease activity over years. Gastroenterology 1994; 107:3-11.

Rachmilewitz D. Coated mesalazine (5-aminosalicylic acid) versus sulphasalazine in the treatment of active ulcerative colitis: a randomised trial. BMJ 1989; 298:82-86.

Riegler G, Tartaglione M T, Carratú R, et al. Age-related clinical severity at diagnosis in 1705 patients with ulcerative colitis: Dig Dis Sci 2000; 45:462-5.

Rubin D T, Siegel C A, Kane S V, et al. Impact of ulcerative colitis from patients' and physicians' perspectives: Results from the UC: NORMAL survey. Inflamm Bowel Dis. 2009; 15:581-588.

Thompson A I, Lees C W. Genetics of ulcerative colitis. Inflamm Bowel Dis. 2011:831-48.

Schmitz H, Barmeyer C, Fromm M, et al. Altered tight junction structure contributes to the impaired epithelial barrier function in ulcerative colitis. Gastroenterology 1999; 116:301-9.

Sjöberg M, Walch A, Meshkat M, et al. Infliximab or cyclosporine as rescue therapy in hospitalized patients with steroid-refractory ulcerative colitis: A retrospective observational study. Inflamm Bowel Dis 2011; 10:1002/ibd.21680.

Tighe H, Takabayashi K, Schwartz D, Marsden R, Beck L, Corbeil J, Richman D D, Eiden J J Jr, Spiegelberg H L, Raz E. Conjugation of protein to immunostimulatory DNA results in a rapid, long-lasting and potent induction of cell-mediated and humoral immunity. Eur J. Immunol. 2000 July; 30(7): 1939-47.

Tokunaga T, Yano O, Kuramoto E, Kimura Y, Yamamoto T, Kataoka T, Weinryb R M, Gustaysson J P, Liljeqvist L, et al. A prospective study of the quality of life after pelvic pouch operation. J Am Coll Surg 1995; 180:589-95. Triantafillidis J K, Merikas E, Georgopoulos F. Current and emerging drugs for the treatment of inflammatory bowel disease. Drug Des Devel Ther 2011; 5:185-210.

Turner D, Walsh C M, Steinhart A H, Griffiths A M. Response to corticosteroids in severe ulcerative colitis: a systematic review of the literature and a meta-regression. Clin Gastroenterol Hepatol 2007; 5:103-110.

Wilhelm S M, McKenney K A, Rivait K N, Kale-Pradhan P B. A review of infliximab use in ulcerative colitis. Clin Ther 2008; 30:223-30.

Wine E, Ossa J C, Gray-Owen S D, Sherman P M. Adherent-invasive *Escherichia coli* target the epithelial barrier. Gut Microbes 2010; 1:80-84.

Weinryb R M, Gustaysson J P, Liljeqvist L, et al. A prospective study of the quality of life after pelvic pouch operation. J Am Coll Surg 1995; 180:589-95.

Xavier R J, Podolsky D K. Unravelling the pathogenesis of inflammatory bowel disease. Nature 2007; 448:427-434.

Yamamoto S. Synthetic oligonucleotides with particular base sequences from the cDNA encoding proteins of *Mycobacterium bovis* BCG induce interferons and activate natural killer cells. Microbiol. Immunol. 1992; 36(1): 55-66.

The invention claimed is:

1. A method of treating chronic active ulcerative colitis in a subject that is refractory or responds insufficiently or is intolerant to anti-inflammatory therapy, comprising administering to a patient in need thereof, an effective exposure of an oligonucleotide comprising the sequence 5'-GGAACAGTTCGTCCATGGC-3' (SEQ ID NO:2) and wherein at least one CG dinucleotide is unmethylated, wherein individual doses of said oligonucleotide are administered on two or more separate occasions 4 or more weeks apart.

2. The method of claim 1, wherein at least one nucleotide in said oligonucleotide has a backbone modification.

3. The method of claim 2, wherein said backbone modification is a phosphate backbone modification represented by a phosphorothioate or a phosphorodithioate modification.

4. The method of claim 3, wherein said phosphate backbone modification is located in the 5'- and/or the 3'-end of said oligonucleotide.

5. The method of claim 1, wherein said oligonucleotide has the sequence 5'-G*G*A*ACAGTTCGTCCAT*G*G*C-3' (SEQ ID NO:1), wherein the CG dinucleotide is unmethylated.

6. The method of claim 1, wherein said two or more separate occasions are 4 to 8 weeks apart.

7. The method according to claim 1, wherein individual doses of said oligonucleotide are administered on three separate occasions 4 weeks apart.

8. The method of claim 1, wherein individual doses of said oligonucleotide are administered on two separate occasions 4 weeks apart.

9. The method of claim 1, wherein the amount of each individual dose of said oligonucleotide is in the range from about 0.3 mg to about 100 mg.

10. The method of claim 1, wherein the amount of each individual dose of said oligonucleotide is in the range from about 25 mg to about 60 mg.

11. The method of claim 1, wherein the amount of each individual dose of said oligonucleotide is about 30 mg.

12. The method of claim 1, wherein said composition is administered as an add-on to a current therapy.

13. The method of claim 1, wherein said oligonucleotide is administered topically to mucosal membranes.

14. The method of claim 1, wherein said oligonucleotide is administered intracolonically.

15. The method of claim 1, wherein said subject is elective for colectomy.

16. The method of claim 15, wherein said colectomy is prevented or delayed.

17. A method of treating chronic active ulcerative colitis in a subject that is refractory or responds insufficiently or is intolerant to anti-inflammatory therapy, the method comprising: administering to the subject an oligonucleotide comprising the sequence 5'-GGAACAGTTCGTC-CATGGC-3' (SEQ ID NO:2), wherein at least one CG dinucleotide is unmethylated, and wherein individual doses of 30 mg each of the oligonucleotide are administered on two or more separate occasions 4 or more weeks apart.

* * * * *